United States Patent [19]
Mao et al.

[11] Patent Number: 5,912,225
[45] Date of Patent: Jun. 15, 1999

[54] BIODEGRADABLE POLY (PHOSPHOESTER-CO-DESAMINOTYROSYL L-TYROSINE ESTER) COMPOUNDS, COMPOSITIONS, ARTICLES AND METHODS FOR MAKING AND USING THE SAME

[75] Inventors: Hai-quan Mao, Towson; Kam W. Leong, Ellicott City, both of Md.

[73] Assignee: Johns Hopkins Univ. School of Medicine, Baltimore, Md.

[21] Appl. No.: 08/834,164

[22] Filed: Apr. 14, 1997

[51] Int. Cl.$^6$ .................................................. C07C 219/00
[52] U.S. Cl. .................................................. 514/2
[58] Field of Search .................................................. 514/2

[56] References Cited

U.S. PATENT DOCUMENTS

| | | |
|---|---|---|
| 3,927,231 | 12/1975 | Desitter et al. . |
| 3,932,566 | 1/1976 | Reader . |
| 4,259,222 | 3/1981 | Login et al. . |
| 4,315,847 | 2/1982 | Login et al. . |
| 4,315,969 | 2/1982 | Login et al. . |
| 4,638,045 | 1/1987 | Kohn et al. . |
| 5,099,060 | 3/1992 | Kohn et al. . |
| 5,194,581 | 3/1993 | Leong . |
| 5,219,564 | 6/1993 | Zalipsky et al. . |
| 5,256,765 | 10/1993 | Leong . |
| 5,530,093 | 6/1996 | Engelhardt et al. . |

FOREIGN PATENT DOCUMENTS

| | | |
|---|---|---|
| 597473 | 5/1960 | Canada . |

OTHER PUBLICATIONS

Langer et al., "Controlled Release of Bioactive Agents", *Rev. Macro. Chem. Phys.,* C23(1), 61–125 (1983).

Chien, Y.W. et al., *Novel Drug Delivery Systems* (1982).

Ertel et al., "Evaluation of Poly(DTH Carbonate), a Tyrosine–derived Degradable Polymer, for Orthopedic Applications", *Journal of Biomedical Materials Research,* 29:1337–48 (1995).

Choueka et al., "Canine Bone Response to Tyrosine–derived Polycarbonates and Poly(L–lactic Acid)", *Journal of Biomedical Materials Research,* 31:35–41 (1996).

Leong et al., "Polyanhydrides for Controlled Release of Bioactive Agents", *Biomaterials,* 7:364 (1986).

*Controlled Release of Bioactive Materials* (Baker et al. ed. 1980).

Bruin et al., "Biodegradable Lysine Diisocyanate–based Poly(glycolide–co–ε–caprolactone)–urethane Network in Artificial Skin", *Biomaterials,* 11 (4) :291–95 (1990).

Penczek et al., "Phosphorus–Containing Polymers", *Handbook of Polymer Synthesis,* Part B, Chpt. 17, 1077–1132 (Kricheldorf ed. 1992).

Kadiyala et al., "Poly(phosphoesters): Synthesis, Physico–chemical Characterization and Biological Response", *Biomedical Applications of Synthetic Biodegradable Polymers,* Chpt. 3, 33–55 (Hollinger ed. 1995).

*Primary Examiner*—Cecilia J. Tsang
*Assistant Examiner*—Patrick R. Delaney
*Attorney, Agent, or Firm*—Matthew P. Vinceint; Kingsley Taft; Foley, Hoag & Eliot LLP

[57] ABSTRACT

Biodegradable polymers are described comprising the recurring monomeric units shown in formula I:

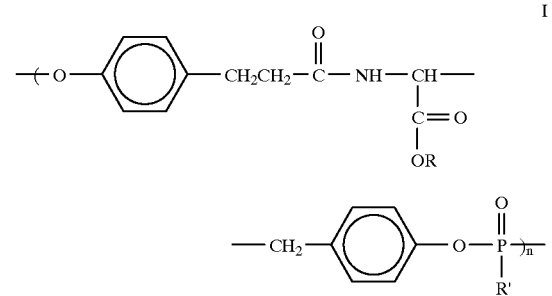

wherein:
  R is selected from the group consisting of H, alkyl, aryl or heterocyclic; and
  R' is selected from the group consisting of H, alkyl, alkoxy, aryl, aryloxy, heterocyclic or heterocycloxy; and
  n is 5 to 500,
wherein said biodegradable polymer is biocompatible before and upon biodegradation.

Processes for preparing the polymers, compositions containing the polymers and biologically active substances, articles useful for implantation or injection into the body fabricated from the compositions, and methods for controllably releasing biologically active substances using the polymers, are also described.

78 Claims, 2 Drawing Sheets

BIODEGRADABLE POLY (PHOSPHOESTER-CO-DESAMINOTYROSYL L-TYROSINE ESTER) COMPOUNDS, COMPOSITIONS, ARTICLES AND METHODS FOR MAKING AND USING THE SAME

BACKGROUND OF THE INVENTION

1. Field of the Invention

The present invention relates to biodegradable polymer compositions, in particular those containing both phosphate and desaminotyrosyl L-tyrosine ester linkages in the polymer backbone and that degrade in vivo into non-toxic residues. The polymers of the invention are particularly useful as implantable medical devices and drug delivery systems.

2. Description of the Prior Art

Biocompatible polymeric materials have been used extensively in therapeutic drug delivery and medical implant device applications. Sometimes, it is also desirable for such polymers to be, not only biocompatible, but also biodegradable to obviate the need for removing the polymer once its therapeutic value has been exhausted.

Conventional methods of drug delivery, such as frequent periodic dosing, are not ideal in many cases. For example, with highly toxic drugs, frequent conventional dosing can result in high initial drug levels at the time of dosing, often at near-toxic levels, followed by low drug levels between doses that can be below the level of their therapeutic value. However, with controlled drug delivery, drug levels can be more nearly maintained at therapeutic, but non-toxic, levels by controlled release in a predictable manner over a longer term.

If a biodegradable medical device is intended for use as a drug delivery or other controlled-release system, using a polymeric carrier is one effective means to deliver the therapeutic agent locally and in a controlled fashion, see Langer et al., *Rev. Macro. Chem. Phys.*, C23(1), 61 (1983). As a result, less total drug is required, and toxic side effects can be minimized. Polymers have been used as carriers of therapeutic agents to effect a localized and sustained release. See Chien et al., *Novel Drug Delivery Systems* (1982). Such delivery systems offer the potential of enhanced therapeutic efficacy and reduced overall toxicity.

For a non-biodegradable matrix, the steps leading to release of the therapeutic agent are water diffusion into the matrix, dissolution of the therapeutic agent, and diffusion of the therapeutic agent out through the channels of the matrix. As a consequence, the mean residence time of the therapeutic agent existing in the soluble state is longer for a non-biodegradable matrix than for a biodegradable matrix, for which passage through the channels of the matrix, while it may occur, is no longer required. Since many pharmaceuticals have short half-lives, therapeutic agents can decompose or become inactivated within the non-biodegradable matrix before they are released. This issue is particularly significant for many bio-macromolecules and smaller polypeptides, since these molecules are generally hydrolytically unstable and have low permeability through a polymer matrix. In fact, in a non-biodegradable matrix, many bio-macromolecules aggregate and precipitate, blocking the channels necessary for diffusion out of the carrier matrix.

These problems are alleviated by using a biodegradable matrix that, in addition to some diffusional release, also allows controlled release of the therapeutic agent by degradation of the polymer matrix. Examples of classes of synthetic polymers that have been studied as possible biodegradable materials include polyesters (Pitt et al., *Controlled Release of Bioactive Materials*, (Baker, ed. 1980); polyamides; polyurethanes; polyorthoesters (Heller et al., *Polymer Engineering Sci.*, 21:727 (1981); and polyanhydrides (Leong et al., *Biomaterials* 7:364 (1986). Specific examples of biodegradable materials that are used as medical implant materials are polylactide, polyglycolide, polydioxanone, poly(lactide-co-glycolide), poly(glycolide-co-polydioxanone), polyanhydrides, poly(glycolide-co-trimethylene carbonate), and poly(glycolide-co-caprolactone).

Polymers having phosphate linkages, called poly (phosphates), poly(phosphonates) and poly(phosphites), are known. The respective structures of these three classes of compounds, each having a different sidechain connected to the phosphorus atom, are as follows:

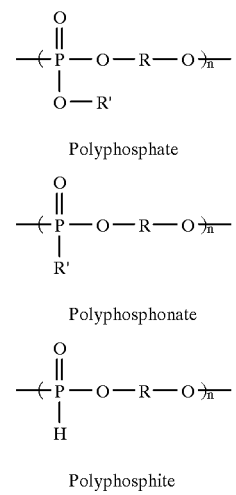

Polyphosphate

Polyphosphonate

Polyphosphite

The versatility of these polymers comes from the versatility of the phosphorus atom, which is known for a multiplicity of reactions. Its bonding can involve the 3p orbitals or various 3s-3p hybrids; spd hybrids are also possible because of the accessible d orbitals. Thus, the physicochemical properties of the poly(phosphoesters) can be readily changed by varying either the R or R' group. The biodegradability of the polymer is due primarily to the physiologically labile phosphoester bond in the backbone of the polymer. By manipulating the backbone or the sidechain, a wide range of biodegradation rates are attainable.

An additional feature of poly(phosphoesters) is the availability of functional side groups. Because phosphorus can be pentavalent, drug molecules or other biologically active substances can be chemically linked to the polymer, as shown by Leong, U.S. Pat. Nos. 5,194,581 and 5,256,765. For example, drugs with —O—carboxy groups may be coupled to the phosphorus via an ester bond, which is hydrolyzable. The P—O—C group in the backbone also lowers the glass transition temperature of the polymer and, importantly, confers solubility in common organic solvents, which is desirable for easy characterization and processing.

Kohn et al., U.S. Pat. No. 4,638,045, discloses bioerodible polymers comprising monomer units of two or three amino acids polymerized via hydrolytically labile bonds at their respective side chains, rather than at the amino- or carboxylic acid-terminals by amide bonds. Zalipsky et al., U.S. Pat. No. 5,219,564, discloses copolymers of poly(alkylene oxides) and amino acids having pendent functional groups capable of being conjugated with pharmaceutically active compounds for drug delivery systems.

Kohn et al., U.S. Pat. No. 5,099,060, describes a particularly preferred monomer for making amino-acid derived poly(iminocarbonates) as:

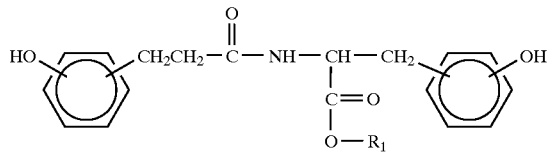

The resulting poly(iminocarbonate) type polymers are said to be hydrolytically unstable and yet exhibit improved thermal stability for convenient processing. Similar tyrosine-derived poly(carbonate) compounds have been reported as promising orthopedic implant materials. Ertel et al., "Evaluation of Poly(DTH Carbonate), a Tyrosine-derived Degradable Polymer, for Orthopedic Applications", *J. of Biomed. Materials Res.*, 29:1337–48 (1995); and Choueka et al., "Canine Bone Response to Tyrosine-derived Polycarbonates and Poly(L-lactic Acid)", *J. of Biomed. Materials Res.*, 31:35–41 (1996). However, there has been a need for materials to degreade at a significantly higher rate than desaminotyrosyl L-tyrosine based poly (iminocarbonates), and none of these documents suggests the use of phosphoester linkages in combination with amino acid-derived monomeric units for this purpose.

SUMMARY OF THE INVENTION

The biodegradable polymers of the invention comprise the recurring monomeric units shown in formula I:

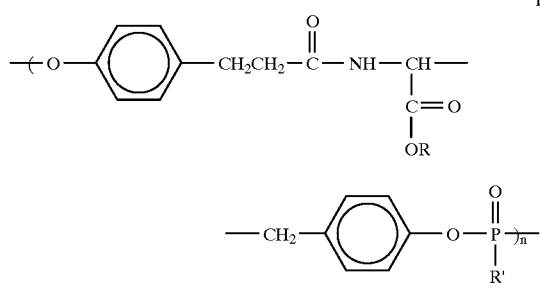

wherein:
R is selected from the group consisting of H, alkyl, aryl or heterocyclic; and
R' is selected from the group consisting of H, alkyl, alkoxy, aryl, aryloxy, heterocyclic or heterocycloxy; and
n is 5 to 500,
wherein the biodegradable polymer is biocompatible before and upon biodegradation.

In another embodiment, the invention comprises polymer compositions comprising:
(a) at least one biologically active substance and
(b) a polymer having the recurring monomeric units shown in formula I.

In yet another embodiment of the invention, an article useful for implantation, injection, or otherwise placed totally or partially within the body, comprises the biodegradable polymer of formula I or the above-described polymer composition.

In a further embodiment, the invention contemplates a process for preparing a biodegradable polymer, comprising the step of reacting an amino acid derivative having formula II:

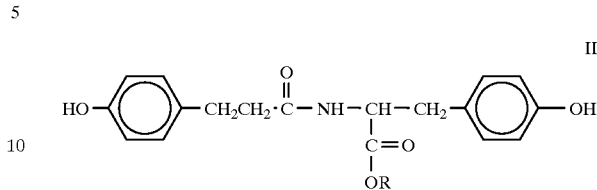

wherein R is as defined above, with a phosphodihalidate of formula III:

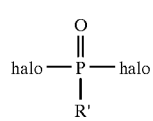

where "halo" is Br, Cl or I, and R' is as defined above, to form the polymer of formula I.

In a still further embodiment of the invention, a method is provided for the controlled release of a biologically active substance comprising the steps of:

(a) combining the biologically active substance with a biodegradable polymer having the recurring monomeric units shown in formula I to form an admixture;

(b) forming the admixture into a shaped, solid article; and (c) implanting or injecting the solid article in vivo at a preselected site, such that the solid implanted or injected article is in at least partial contact with a biological fluid.

DETAILED DESCRIPTION OF THE INVENTION

Polymers of the Invention

Figure 1:
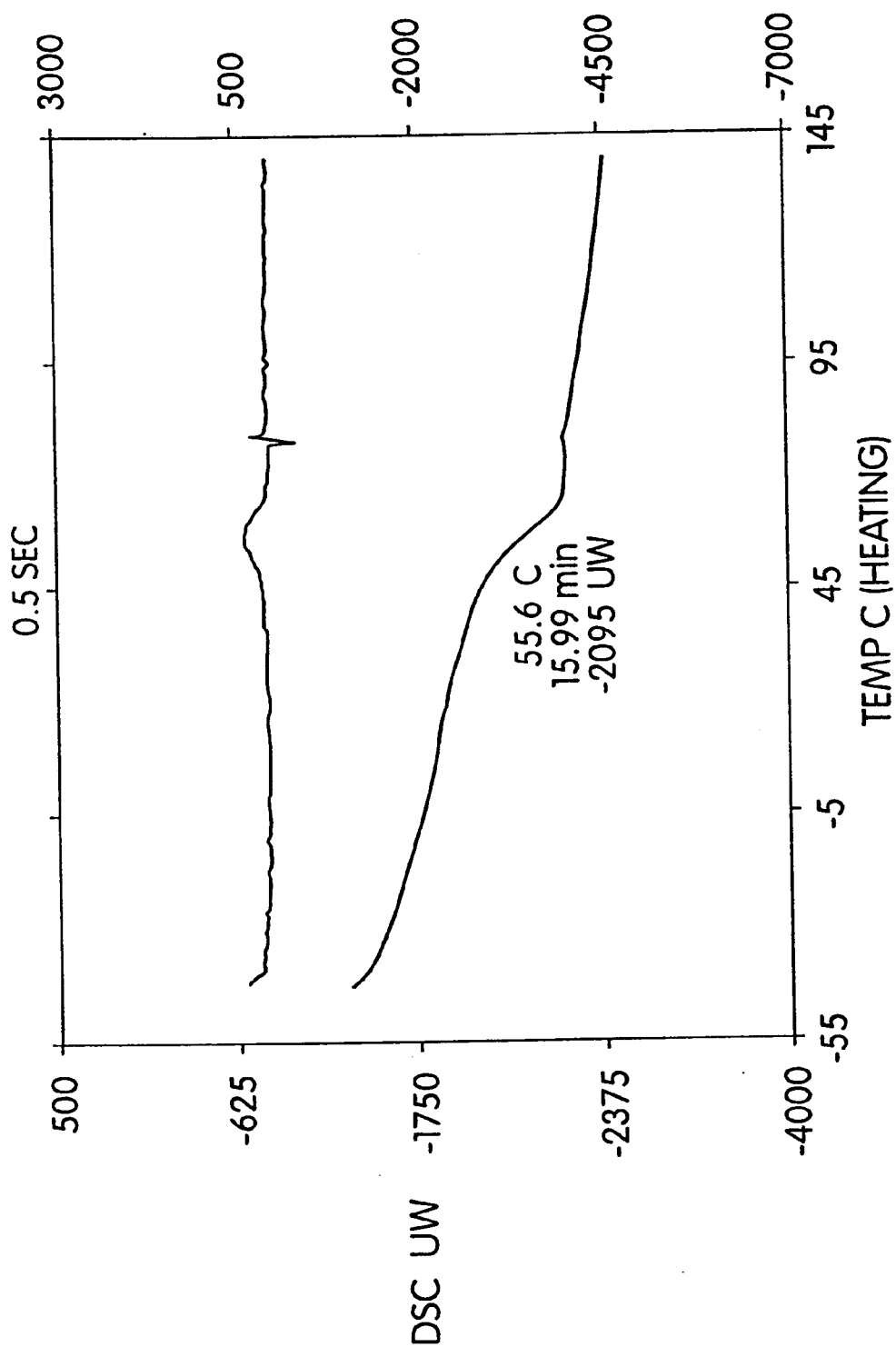
FIG. 1 shows the differential scanning calorimetry data for a polymer of the invention.

As used herein, the term "aliphatic" refers to a linear, branched, cyclic alkane, alkene, or alkyne. Preferred aliphatic groups in the poly(phosphoester-co-amide) polymer of the invention are linear or branched and have from 1 to 20 carbon atoms.

As used herein, the term "aryl" refers to an unsaturated cyclic carbon compound with $4n+2\pi$ electrons.

As used herein, the term "heterocyclic" refers to a saturated or unsaturated ring compound having one or more atoms other than carbon in the ring, for example, nitrogen, oxygen or sulfur.

The biodegradable polymer of the invention comprises the recurring monomeric units shown in formula I:

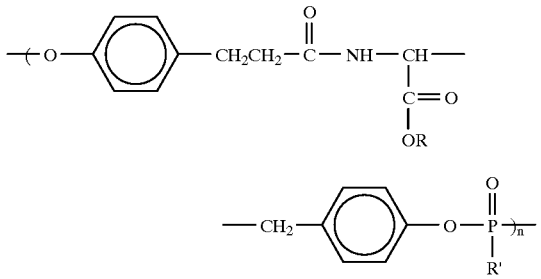

wherein R is selected from the group consisting of H, alkyl, aryl or heterocyclic, preferably a branched or straight chain aliphatic group having from 1–20 carbon atoms. R can be any aliphatic moiety so long as it does not interfere undesirably with the polymerization or biodegradation reactions of the polymer. Specifically, R can be an alkyl group, such as methyl, ethyl, 1,2-dimethylethyl, n-propyl, isopropyl, 2,2-dimethylpropyl or tert-butyl, n-pentyl, tert-pentyl, n-hexyl, n-heptyl and the like; an alkyl group substituted with a non-interfering substituent, for example, halogen-substituted alkyl; or a cycloaliphatic group such as cyclopentyl, 2-methylcyclopentyl, cyclohexyl, cyclohexenyl and the like. Preferably, however, R is a branched or straight chain alkyl group and, even more preferably, an alkyl group having from 2 to 18 carbon atoms. Most preferably, R is an n-hexyl group.

R' in the polymer of the invention is an alkyl, alkoxy, aryl, aryloxy, heterocyclic or heterocycloxy residue. Examples of useful alkyl R' groups include methyl, ethyl, n-propyl, i-propyl, n-butyl, tert-butyl, —$C_8H_{17}$, and the like groups; alkyl substituted with a non-interfering substituent, such as a halogen group; corresponding alkoxy groups; and alkyl that is conjugated with a biologically active substance to form a pendant drug delivery system.

When R' is aryl or the corresponding aryloxy group, it typically contains from about 5 to about 14 carbon atoms, preferably about 5 to 12 carbon atoms and, optionally, can contain one or more rings that are fused to each other. Examples of particularly suitable aromatic groups include phenyl, phenoxy, naphthyl, anthracenyl, phenanthrenyl and the like.

When R' is heterocyclic or heterocycloxy, it typically contains from about 5 to 14 ring atoms, preferably from about 5 to 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. Preferably, when R' is heterocyclic or heterocycloxy, it is selected from the group consisting of furan, pyridine, N-alkylpyridine, 1,2,3- and 1,2,4-triazoles, indene, anthracene and purine rings.

In a particularly preferred embodiment, R' is an alkyl group, an alkoxy group, a phenyl group, a phenoxy group, or a heterocycloxy group and, even more preferably, an alkoxy group having from 1 to 7 carbon atoms. Most preferably, R' is an ethoxy group.

The number n can vary greatly depending on the biodegradability and the release characteristics desired in the polymer, but typically varies between about 2 and 500. Preferably, n is from about 5 to about 300 and, most preferably, from about 5 to about 200.

Biodegradable polymers differ from non-biodegradable polymers in that they can be degraded during in vivo therapy. This generally involves breaking down the polymer into its monomeric subunits. In principle, the ultimate hydrolytic breakdown products of a polymer of the invention are desaminotyrosyl tyrosine (which is derived from the naturally occurring amino acid L-tyrosine and its analog, desaminotyrosine, which occurs naturally in plants), an aliphatic alcohol, and phosphate. All of these degradation products are potentially non-toxic. However, the intermediate oligomeric products of the hydrolysis may have different properties. Thus, toxicology of a biodegradable polymer intended for implantation or injection, even one synthesized from apparently innocuous monomeric structures, is typically determined after one or more toxicity analyses.

A typical in vitro toxicity assay would be performed with live carcinoma cells, such as GT3TKB tumor cells, in the following manner:

200 $\mu$L of various concentrations of suspensions of the test monomer or polymers are placed in 96-well tissue culture plates seeded with human gastric carcinoma cells (GT3TKB) at $10^4$/well density. The degraded polymer products are incubated with the GT3TKB cells for 48 hours. The results of the assay can be plotted as % relative growth vs. concentration of degraded polymer in the tissue-culture well.

Polymers for use in medical applications such as implants and prostheses can also be evaluated by well-known in vivo tests, such as subcutaneous implantations in rats to confirm that they hydrolyze without significant levels of irritation or inflammation at the subcutaneous implantation sites.

The biodegradable polymer of the invention is preferably sufficiently pure to be biocompatible itself and remains biocompatible upon biodegradation. By "biocompatible" is meant that the biodegradation products or the polymer itself are nontoxic and result in only minimal tissue irritation when implanted or injected into vasculated tissue.

Figure 2:
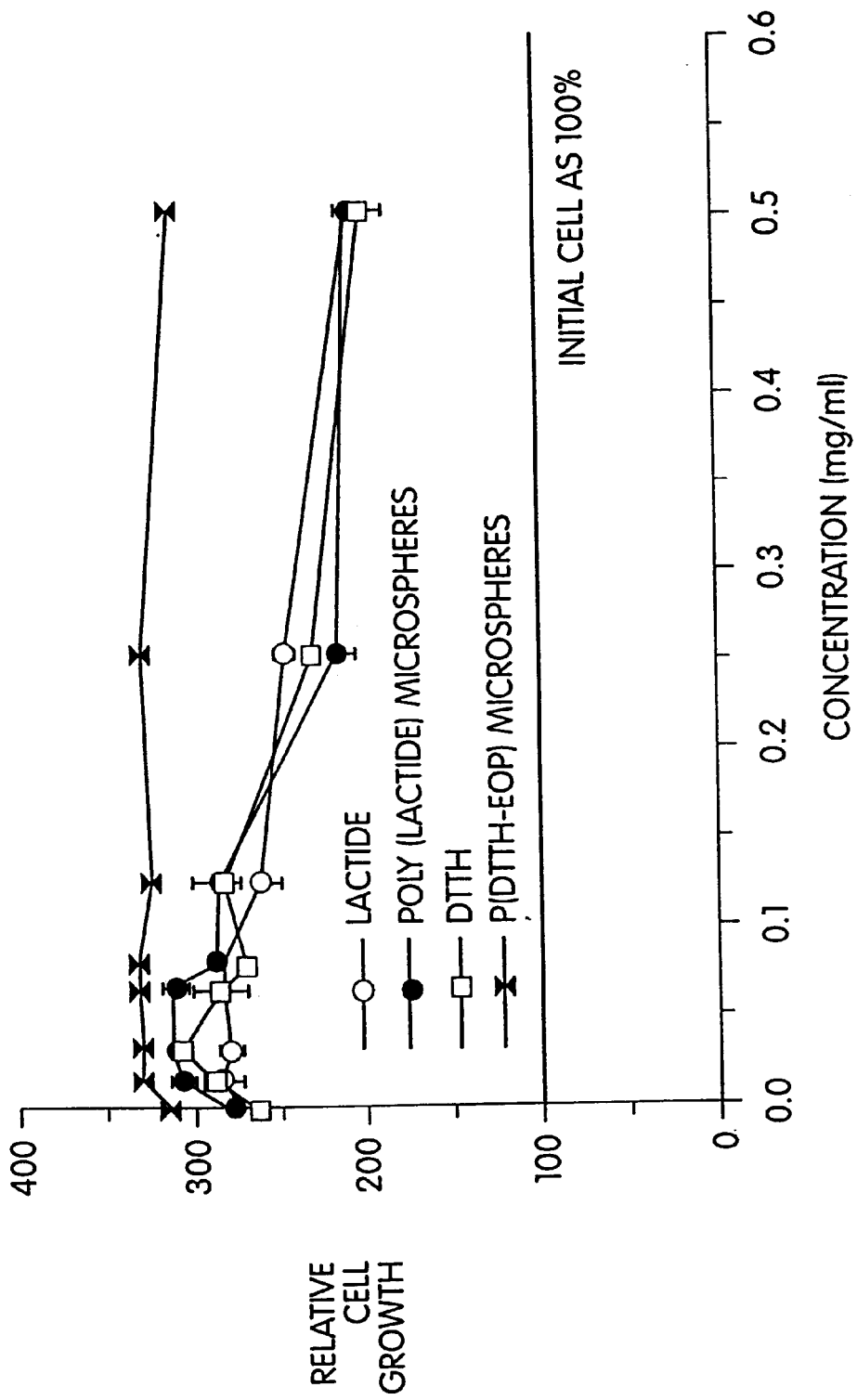
FIG. 2 shows a toxicity assay plot of relative cell growth (%) versus concentration in a tissue-culture well (mg/ml) for four separate polymer samples--DTTH, P(DTTH-EOP), L-lactide and poly(L-lactide).

The in vitro cytotoxicity profile for desaminotyrosyl L-tyrosine hexyl ester ("DTTH"), a monomer used to make a particularly preferred polymer of the invention, and the corresponding polymer P(DTTH-EOP), in microsphere form, as compared with those of a comparison monomer commonly used in biodegradable materials, L-lactide and poly(L-lactide), also in solid and microsphere form, is shown in FIG. 2.

The polymer of the invention is preferably soluble in one or more common organic solvents for ease of fabrication and processing. Common organic solvents include such solvents as ethanol, chloroform, dichloromethane, acetone, ethyl acetate, DMAC, N-methyl pyrrolidone, dimethylformamide, and dimethylsulfoxide. The polymer is preferably soluble in at least one of the above solvents.

The polymer of the invention can also comprise additional biocompatible monomeric units so long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly (iminocarbonates); and polyanhydrides.

Synthesis of Poly(phosphoester-co-amide) Polymers

The most common general reaction in preparing poly-(phosphates) is a dehydrochlorination between a phosphodichloridate and a diol according to the following equation:

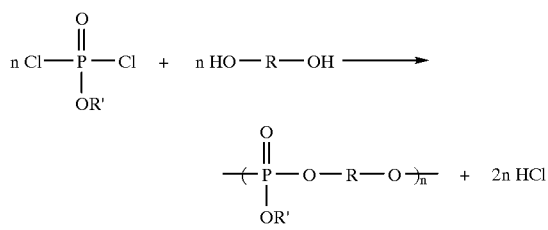

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature.

An advantage of melt polycondensation is that it avoids the use of solvents and large amounts of other additives, thus making purification more straightforward. It can also provide polymers of reasonably high molecular weight. Somewhat rigorous conditions, however, are often required and can lead to chain acidolysis (or hydrolysis if water is present). Unwanted, thermally-induced side reactions, such as cross-linking reactions, can also occur if the polymer backbone is susceptible to hydrogen atom abstraction or oxidation with subsequent macroradical recombination.

To minimize these side reactions, the polymerization can also be carried out in solution. Solution polycondensation requires that both the prepolymer and the phosphorus component be soluble in a common solvent. Typically, a chlorinated organic solvent is used, such as chloroform, dichloromethane, or dichloroethane. The solution polymerization must be run in the presence of equimolar amounts of the reactants and, preferably, a stoichiometric amount of an acid acceptor or a Lewis acid-type catalyst. Useful acid acceptors include a tertiary amines such as pyridine or triethylamine. Examples of useful Lewis acid-type catalysts include magnesium chloride and calcium chloride. The product is then typically isolated from the solution by precipitation in a non-solvent and purified to remove the hydrochloride salt by conventional techniques known to those of ordinary skill in the art, such as by washing with an aqueous acidic solution, e.g., dilute HCl.

Reaction times tend to be longer with solution polymerization than with melt polymerization. However, because overall milder reaction conditions can be used, side reactions are minimized, and more sensitive functional groups can be incorporated into the polymer. The disadvantages of solution polymerization are that the attainment of high molecular weights, such as a Mw greater than 20,000, is less likely.

Interfacial polycondensation can be used when high molecular weight polymers are desired at high reaction rates. Mild conditions minimize side reactions. Also the dependence of high molecular weight on stoichiometric equivalence between diol and dichloridate inherent in solution methods is removed. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, can be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In a preferred embodiment of the invention, the biodegradable polymer of formula I is made by a process comprising the step of reacting an amino acid derivative known as a desaminotyrosyl L-tyrosine ester, which has the formula II:

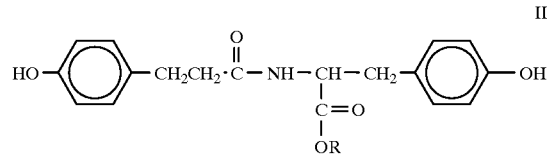

wherein R is as defined above, with a phosphodihalidate of formula III:

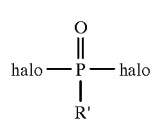

where "halo" is Br, Cl or I, and R' is as defined above, to form the polymer of formula I.

The desaminotyrosyl L-tyrosine ester of formula II can be prepared by dicyclohexylcarbodiimide (DCC)-mediated coupling reactions in an inert solvent following standard procedures of peptide chemistry, such as disclosed in Bodanszky, *Practice of Peptide Synthesis*, 145 (1984), the disclosure of which is hereby incorporated by reference. As a specific example, the hexyl ester of desaminotyrosyl L-tyrosine ester ("DTTH") can be prepared by the DCC-mediated coupling of desaminotyrosine and tyrosine hexyl ester in tetrahydrofuran as the solvent. The crude alkyl ester is typically obtained as an oil, which can be purified by a number of methods, e.g., flash chromatography on silica gel with 70:30 chloroform:ethyl acetate or 98:2 methylene chloride:methanol. Crystallization of the pure DTTH can usually be accelerated by crystal seeding.

Alkyl esters of tyrosine having up to eight carbon atoms in the ester group can be prepared by the procedure disclosed in Greenstein et al., *Chemistry of the Amino Acids*, 929 (1961), particularly Illustrative Procedure 10–48, the disclosure of which is hereby incorporated by reference. Alkyl esters of tyrosine having more than eight carbon atoms in the ester group can be prepared according to the procedure disclosed in the examples of Overell, U.S. Pat. No. 4,428,932, which is hereby incorporated by reference.

The purpose of the polymerization reaction of the invention is to form a copolymer comprising (i) desaminotyrosyl L-desaminotyrosine recurring units derived from the amino acid derivative of formula II and (ii) phosphorylated ester recurring units. The result can be a copolymer having a microcrystalline structure that is particularly well-suited to use as a controlled release carrier.

The process of the invention can take place at widely varying temperatures, depending upon whether a solvent is used and, if so, which one; the molecular weight desired; the susceptibility of the reactants to form side reactions; and the presence of a catalyst. Preferably, however, the process takes place at a temperature ranging from about 0 to about +235° C. for melt conditions. Somewhat lower temperatures, e.g., for example from about −50 to about 100° C. may be possible with solution polymerization or with the use of either a cationic or anionic catalyst.

The time required for the process also can vary widely, depending on the type of reaction being used, the molecular weight desired and, in general, the need to use more or less rigorous conditions for the reaction to proceed to the desired degree of completion. Typically, however, the process takes place during a time between about 30 minutes and 7 days.

While the process may be in bulk, in solution, by interfacial polycondensation, or any other convenient method of polymerization, preferably, the process takes place under solution conditions. Particularly useful solvents include methylene chloride, chloroform, tetrahydrofuran, dimethyl formamide, dimethyl sulfoxide or any of a wide variety of inert organic solvents.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. The most preferred acid acceptor is the substituted aminopyridine 4-dimethylaminopyridine ("DMAP").

The polymer of formula I is isolated from the reaction mixture by conventional techniques, such as by precipitating out, extraction with an immiscible solvent, evaporation, filtration, crystallization and the like. Typically, however, the polymer of formula I is both isolated and purified by quenching a solution of polymer with a non-solvent or a partial solvent, such as diethyl ether or petroleum ether.

Biodegradability and Release Characteristics

The polymer of formula I is usually characterized by a release rate of the biologically active substance in vivo that is controlled at least in part as a function of hydrolysis of the phosphoester bond of the polymer during biodegradation. Additionally, the biologically active substance to be released may be conjugated to the phosphorus sidechain R' to form a pendant drug delivery system. Further, other factors are also important.

The life of a biodegradable polymer in vivo also depends upon its molecular weight, crystallinity, biostability, and the degree of cross-linking. In general, the greater the molecular weight, the higher the degree of crystallinity, and the greater the biostability, the slower biodegradation will be.

Accordingly, the structure of the sidechain can influence the release behavior of compositions comprising a biologically active substance. For example, it is expected that conversion of the phosphate sidechain to a more lipophilic, more hydrophobic or bulky group would slow down the degradation process. Thus, release is usually faster from polymer compositions with a small aliphatic group sidechain than with a bulky aromatic sidechain.

The mechanical properties of the polymer are also important with respect to the processability in making molded or pressed articles for implantation. For example, the glass transition temperature can vary widely but must be sufficiently lower than the temperature of decomposition to accommodate conventional fabrication techniques, such as compression molding, extrusion or injection molding. The polymers of the invention typically have glass transition temperatures varying between about 25 to about 75° C. and, preferably, from about 45 to about 65° C.

Weight-average molecular weights (Mw) typically vary from about 2,000 to about 200,000 daltons, preferably from about 2,000 to about 100,000 daltons and, most preferably, from about 2,000 to about 20,000 daltons. Number average molecular weights (Mn) can also vary widely, but generally fall in the range of about 1,000 to 100,000, preferably about 1,000 to 50,000 and, most preferably, from about 1,000 to about 10,000. Intrinsic viscosities generally vary from about 0.01 to about 2.0 dL/g in chloroform at 40° C., preferably from about 0.01 to about 1.0 dL/g and, most preferably, about 0.01 to about 0.5 dL/g.

Polymer Compositions

The polymer of formula I can be used either alone or as a composition containing, in addition, a biologically active substance to form a variety of useful biodegradable materials. For example, the polymer of formula I can be used to produce a biosorbable suture, an orthopedic appliance or bone cement for repairing injuries to bone or connective tissue, a laminate for degradable or non-degradable fabrics, or a coating for an implantable device, even without the presence of a biologically active substance.

Preferably, however, the biodegradable polymer composition comprises both:

(a) at least one biologically active substance and
(b) the polymer having the recurring monomeric units shown in formula I where R, R' and n are as defined above.

The biologically active substance of the invention can vary widely with the purpose for the composition. The active substance(s) may be described as a single entity or a combination of entities. The delivery system is designed to be used with biologically active substances having high water-solubility as well as with those having low water-solubility to produce a delivery system that has controlled release rates. The term "biologically active substance" includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

Non-limiting examples of useful biologically active substances include the following expanded therapeutic categories: anabolic agents, antacids, anti-asthmatic agents, anti-cholesterolemic and anti-lipid agents, anti-coagulants, anti-convulsants, anti-diarrheals, anti-emetics, anti-infective agents, anti-inflammatory agents, anti-manic agents, anti-nauseants, anti-neoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, antigenic materials, and prodrugs.

Specific examples of useful biologically active substances from the above categories include: (a) anti-neoplastics such as androgen inhibitors, antimetabolites, cytotoxic agents, immunomodulators; (b) anti-tussives such as dextromethorphan, dextromethorphan hydrobromide, noscapine, carbetapentane citrate, and chlophedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (f) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines and other bioactive peptidic compounds, such as hGH, tPA, calcitonin, ANF, EPO and insulin; (n) anti-infective agents such as anti-fungals, anti-virals, antiseptics and antibiotics; and (o) antigenic materials, partricularly those useful in vaccine applications.

Preferably, the biologically active substance is selected from the group consisting of polysaccharides, growth factors, hormones, anti-angiogenesis factors, interferons or cytokines, and pro-drugs. In a particularly preferred embodiment, the biologically active substance is a therapeutic drug or pro-drug, most preferably a drug selected from the group consisting of chemotherapeutic agents and other anti-neoplastics, antibiotics, anti-virals, anti-fungals, anti-inflammatories, anticoagulants, an antigenic materials.

The biologically active substances are used in amounts that are therapeutically effective. While the effective amount of a biologically active substance will depend on the particular material being used, amounts of the biologically active substance from about 1% to about 65% have been easily incorporated into the present delivery systems while achieving controlled release. Lesser amounts may be used to achieve efficacious levels of treatment for certain biologically active substances.

In addition, the polymer composition of the invention can also comprise polymer blends of the polymer of the invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for structural implants such as for orthopedic applications. Examples of such additional biocompatible polymers include other polycarbonates; polyesters; polyorthoesters; polyamides; polyurethanes; poly(iminocarbonates); and polyanhydrides.

Pharmaceutically acceptable carriers may be prepared from a wide range of materials. Without being limited thereto, such materials include diluents, binders and adhesives, lubricants, disintegrants, colorants, bulking agents, flavorings, sweeteners and miscellaneous materials such as buffers and adsorbents in order to prepare a particular medicated composition.

Implants and Delivery Systems Designed for Injection

In its simplest form, a biodegradable therapeutic agent delivery system consists of a dispersion of the therapeutic agent in a polymer matrix. The therapeutic agent is typically released as the polymeric matrix biodegrades in vivo into soluble products that can be excreted from the body.

In a particularly preferred embodiment, an article is used for implantation, injection, or otherwise placed totally or partially within the body, the article comprising the biodegradable polymer composition of the invention. The biologically active substance of the composition and the polymer of the invention may form a homogeneous matrix, or the biologically active substance may be encapsulated in some way within the polymer. For example, the biologically active substance may be first encapsulated in a microsphere and then combined with the polymer in such a way that at least a portion of the microsphere structure is maintained. Alternatively, the biologically active substance may be sufficiently immiscible in the polymer of the invention that it is dispersed as small droplets, rather than being dissolved, in the polymer. Either form is acceptable, but it is preferred that, regardless of the homogeneity of the composition, the release rate of the biologically active substance in vivo remain controlled, at least partially as a function of hydrolysis of the phosphoester bond of the polymer upon biodegradation.

In a preferred embodiment, the article of the invention is designed for implantation or injection into the body of an animal. It is particularly important that such an article result in minimal tissue irritation when implanted or injected into vasculated tissue.

As a structural medical device, the polymer compositions of the invention provide a physical form having specific chemical, physical, and mechanical properties sufficient for the application and a composition that degrades in vivo into non-toxic residues. Typical structural medical articles include such implants as orthopedic fixation devices, ventricular shunts, laminates for degradable fabric, drug-carriers, biosorbable sutures, burn dressings, coatings to be placed on other implant devices, and the like.

In orthopedic articles, the composition of the invention may be useful for repairing bone and connective tissue injuries. For example, a biodegradable porous material can be loaded with bone morphogenetic proteins to form a bone graft useful for even large segmental defects. In vascular graft applications, a biodegradable material in the form of woven fabric can be used to promote tissue ingrowth. The polymer composition of the invention may be used as a temporary barrier for preventing tissue adhesion, e.g., following abdominal surgery.

On the other hand, in nerve regeneration articles, the presence of a biodegradable supporting matrix can be used to facilitate cell adhesion and proliferation. When the polymer composition is fabricated as a tube for nerve generation, for example, the tubular article can also serve as a geometric guide for axonal elongation in the direction of functional recovery.

As a drug delivery device, the polymer compositions of the invention provide a polymeric matrix capable of sequestering a biologically active substance and provide predictable, controlled delivery of the substance. The polymeric matrix then degrades to non-toxic residues.

Biodegradable medical implant devices and drug delivery products can be prepared in several ways. The polymer can be melt processed using conventional extrusion or injection molding techniques, or these products can be prepared by dissolving in an appropriate solvent, followed by formation of the device, and subsequent removal of the solvent by evaporation or extraction.

Once a medical implant article is in place, it should remain in at least partial contact with a biological fluid, such as blood, internal organ secretions, mucous membranes, cerebrospinal fluid and the like.

EXAMPLES

Example 1
Preparation of the Monomer Desaminotyrosyl L-Tyrosine Hexyl Ester (DTTH)

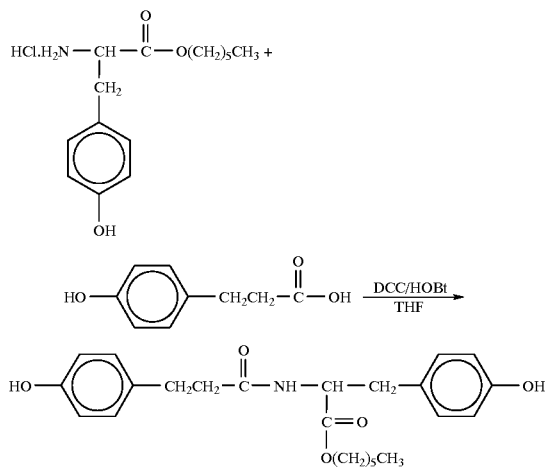

14.15 g of desaminotyrosine, 22.6 g of tyrosine hexyl ester, and 11.51 g of N-hydroxybenzotriazole hydrate ("HOBt") were dissolved in 150 ml tetrahydrofuran and cooled to −10° C. Dicyclohexylcarbodiimide (DCC, 19.33 g) was added with stirring.

The reaction mixture was stirred continuously for four hours. Then 5 ml of glacial acetic acid was added to destroy the unreacted DCC, and the mixture was filtered. The filtrate was evaporated to dryness, and the residue was re-dissolved in 150 ml of ethyl acetate, washed with 0.5N HCl solution (100 ml×3), 0.5N $Na_2CO_3$ solution (100 ml×3), and saturated NaCl solution (100 ml×3), successively. The ethyl acetate solution was dried over anhydrous $MgSO_4$ and evaporated to dryness again.

The crude product was purified by flash column chromatography ($CH_2Cl_2$-methanol, 98:2, v/v). The fractions containing DTTH were evaporated to dryness and redissolved in a small volume of a 95:5 v/v mixture of ethyl acetate-methanol. The DTTH product was gradually crystallized/solidified after an excess of hexane was added. The solid DTTH was removed by filtration and dried under a vacuum to yield about 15–20 g of white powder (43–58% yield).

Example 2
Synthesis of the Corresponding Poly(phosphoester-co-amide) P(DTTH-EOP)

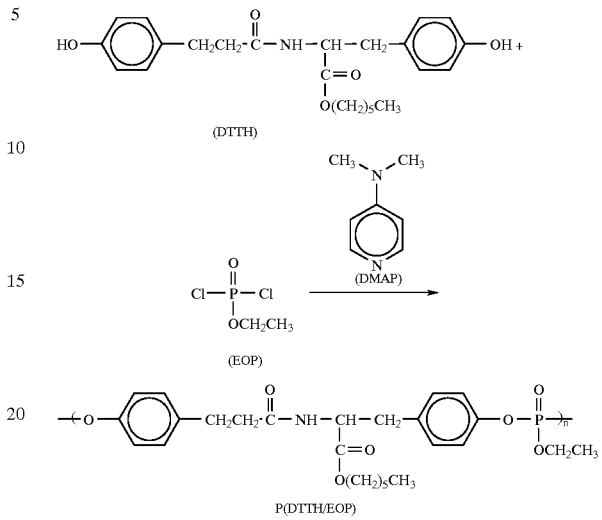

Under an argon stream, 7.8 g of desaminotyrosyl tyrosine hexyl ester (DTTH), 5.07 g of 4-dimethylaminopyridine (DMAP), and 50 ml of methylene chloride were transferred to a 250 ml flask equipped with a funnel. A solution of 3.07 g of ethyl phosphodichloridate (EOP) in 30 ml of methylene chloride was added to the funnel. The solution in the flask was cooled down to −40° C. with stirring, and the EOP solution was added dropwise through the funnel. When the addition was complete, the mixture was gradually brought up to a temperature of 45° C. and was maintained at reflux temperature overnight.

The solvent was then evaporated, and a vacuum (0.1 mm Hg) was applied for one hour while the temperature of the residue was maintained at 120° C. The residue was re-dissolved in 100 ml of chloroform, washed with a 0.1M solution of HCl in distilled water, dried over anhydrous $Na_2SO_4$, and quenched into 500 ml of ether. The resulting precipitate was collected and dried under vacuum, producing a slightly yellow powder.

Example 3
Properties of P(DTTH-EOP)

A P(DTTH-EOP) polymer was prepared as described above in Example 2. The resulting poly(phosphoester-co-amide) polymer was analyzed by GPC using polystyrene as a standard, and the resulting graph established an Mw of 5,450 and an Mn of 1,670. The polydispersity (Mw/Mn) was determined to be 3.27.

The polymer was very soluble in chloroform, dichloromethane, dimethylformamide, and dimethyl sulfoxide; soluble in N-methylpyrrolidone; and swelled in ethanol, methanol, acetone, acetonitrile and tetrahydrofuran. The intrinsic viscosity was measured in chloroform ($CH_3Cl$) at 40° C. and determined to be 0.055 dL/g.

The Tg of the polymer was determined by differential scanning calorimetry ("DSC") to be 55.6° C., as shown in FIG. 1. No melting peak was observed in the DSC curve.

The invention being thus described, it will be obvious that the same may be varied in many ways. Such variations are not to be regarded as a departure from the spirit and scope of the invention, and all such modifications are intended to be included within the scope of the following claims.

We claim:

1. A biodegradable polymer comprising the recurring monomeric units shown in formula I:

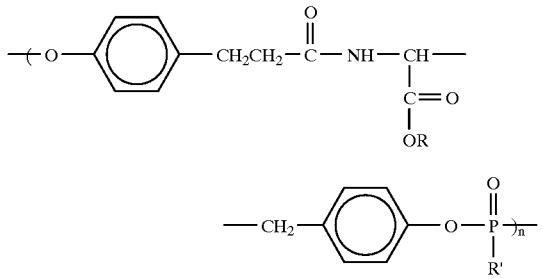

wherein:

R is selected from the group consisting of H, alkyl, aryl and heterocyclic; and

R' is selected from the group consisting of H, alkyl, alkoxy, aryl, aryloxy, heterocyclic and heterocycloxy; and n is 5 to 500, wherein said biodegradable polymer is biocompatible before and upon biodegradation.

2. The polymer of claim 1 wherein R is a branched or straight chain alkyl group.

3. The polymer of claim 2 wherein R has from 2 to 10 carbon atoms.

4. The polymer of claim 1 wherein R is a hexyl group.

5. The polymer of claim 1 wherein R' is an alkyl group, an alkoxy group, a phenyl group, a phenoxy group, or a heterocycloxy group.

6. The polymer of claim 1 wherein R' is an alkoxy group having from 1 to 7 carbon atoms.

7. The polymer of claim 1 wherein R' is an ethoxy group.

8. The polymer of claim 1 wherein the n is between 5 and 300.

9. The polymer of claim 1 wherein Mw is between about 2,000 and 200,000.

10. The polymer of claim 1 wherein said polymer is prepared by solution polymerization.

11. The polymer of claim 1 wherein said polymer comprises additional biocompatible monomeric units.

12. The polymer of claim 1 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

13. A process for preparing a biodegradable polymer comprising the recurring monomeric units of formula I:

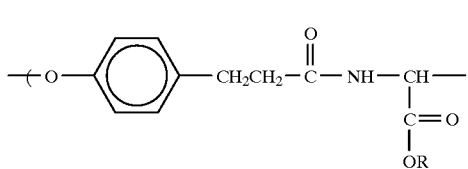

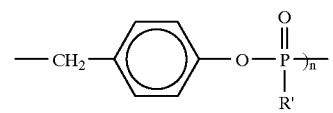

wherein:

R is selected from the group consisting of H, alkyl, aryl and heterocyclic; and

R' is selected from the group consisting of H, alkyl, alkoxy, aryl, aryloxy, heterocyclic and heterocycloxy; and n is 5 to 500, wherein said biodegradable polymer is biocompatible before and upon biodegradation, said process comprising the step of reacting an amino acid derivative having formula II:

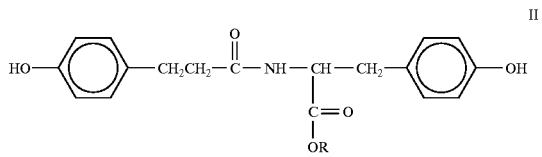

wherein R is as defined above, with a phosphodihalidate of formula III:

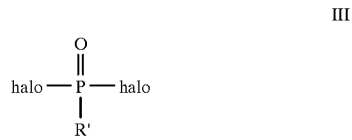

where "halo" is Br, Cl or I, and R' is as defined above, to form the polymer of formula I.

14. The process of claim 13 wherein R is a branched or straight chain alkyl group having from 2 to 18 carbon atoms.

15. The process of claim 13 wherein R is a hexyl group.

16. The process of claim 13 wherein R' is an alkoxy group having from 1 to 7 carbon atoms.

17. The process of claim 13 wherein R' is an ethoxy group.

18. The process of claim 13 wherein n is 5 to 300.

19. The process of claim 13 wherein said process takes place at a temperature about −50 to about +235° C.

20. The process of claim 13 wherein said process takes place during a time between about 30 minutes and seven days.

21. The process of claim 13 wherein said process is a solution polymerization.

22. The process of claim 13 wherein, during the process, an acid acceptor is present.

23. The process of claim 13 wherein said polymer of formula I has an Mw of about 2,000 to about 200,000.

24. The process of claim 13 wherein said polymer of formula I has an Mn of about 1,000 to about 100,000.

25. The process of claim 13 wherein said polymer of formula I is purified by quenching a solution of said polymer with a non-solvent or a partial solvent.

26. A biosorbable suture comprising the polymer of claim 1.

27. An orthopedic appliance, bone cement or bone wax for repairing injuries to bone and connective tissue comprising the polymer of claim 1.

28. A laminate for degradable or non-degradable fabrics comprising the polymer of claim 1.

29. A coating for an implantable device comprising the polymer of claim 1.

30. A biodegradable polymer composition comprising:
(a) at least one biologically active substance and
(b) a polymer having the recurring monomeric units shown in formula I:

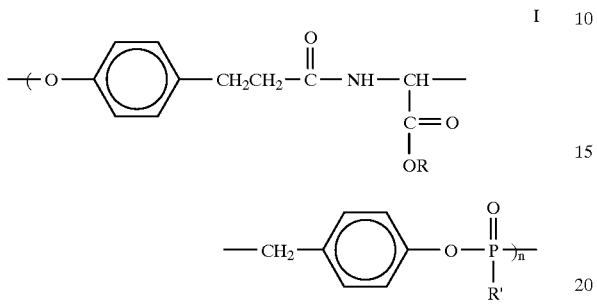

wherein:
R is selected from the group consisting of H, alkyl, aryl and heterocyclic; and
R' is selected from the group consisting of H, alkyl, alkoxy, aryl, aryloxy, heterocyclic and heterocycloxy; and
n is 5 to 500,
wherein said biodegradable polymer is biocompatible before and upon biodegradation.

31. The polymer composition of claim 30 wherein R is a branched or straight chain alkyl group.

32. The polymer composition of claim 30 wherein R is a hexyl group.

33. The polymer composition of claim 30 wherein R' is an alkyl group, an alkoxy group, a phenyl group, a phenoxy group, or a heterocycloxy group.

34. The polymer composition of claim 30 wherein R' is an alkoxy group.

35. The polymer composition of claim 30 wherein n is 5 to 300.

36. The polymer composition of claim 30 wherein said polymer is prepared by solution polymerization.

37. The polymer composition of claim 30 wherein said polymer comprises additional biocompatible monomeric units or is blended with other biocompatible polymers.

38. The polymer composition of claim 30 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

39. The polymer composition of claim 30 wherein said biologically active substance is selected from the group consisting of polysaccharides, growth factors, hormones, anti-angiogenesis factors, interferons or cytokines, and pro-drugs of these substances.

40. The polymer composition of claim 30 wherein said biologically active substance is a therapeutic drug or pro-drug.

41. The polymer composition of claim 40 wherein said drug is selected from the group consisting of anti-neoplastic agents, antibiotics, anti-virals, anti-fungals, anti-inflammatories, and anticoagulants.

42. The polymer composition of claim 30 wherein said biologically active substance and said polymer form a homogeneous matrix.

43. The polymer composition of claim 30 wherein said polymer is characterized by a release rate of the biologically active substance in vivo controlled at least partially as a function of hydrolysis of the phosphoester bond of the polymer during biodegradation.

44. An article useful for implantation, injection, or otherwise placed totally or partially within the body, said article comprising a biodegradable polymer composition comprising:
(a) at least one biologically active substance and
(b) a polymer having the recurring monomeric units shown in formula I:

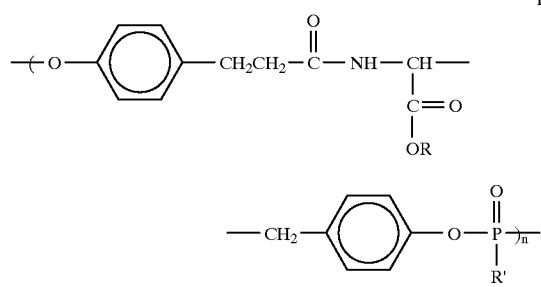

wherein:
R is selected from the group consisting of H, alkyl, aryl and heterocyclic; and
R' is selected from the group consisting of H, alkyl, alkoxy, aryl, aryloxy, heterocyclic and heterocycloxy; and
n is 5 to 500,
wherein said biodegradable polymer is biocompatible before and upon biodegradation.

45. The article of claim 44 wherein R is a branched or straight chain alkyl group.

46. The article of claim 44 wherein each of R has from 5 to 10 carbon atoms.

47. The article of claim 44 wherein R' is an alkyl group, an alkoxy group, a phenyl group, a phenoxy group, or a heterocycloxy group.

48. The article of claim 44 wherein R' is an alkoxy group.

49. The article of claim 44 wherein n is 5 to 300.

50. The article of claim 44 wherein said polymer is prepared by solution polymerization.

51. The article of claim 44 wherein said polymer comprises additional biocompatible monomeric units.

52. The article of claim 44 wherein said polymer is soluble in at least one of the solvents selected from the group consisting of acetone, dimethylene chloride, chloroform, ethyl acetate, DMAC, N-methyl pyrrolidone, dimethylformamide and dimethylsulfoxide.

53. The article of claim 44 wherein said biologically active substance is selected from the group consisting of polysaccharides, growth factors, hormones, anti-angiogenesis factors, interferons or cytokines, and pro-drugs of these substances.

54. The article of claim 44 wherein said biologically active substance is a therapeutic drug or pro-drug.

55. The article of claim 54 wherein said biologically active substance is selected from the group consisting of anti-neoplastic agents, antibiotics, anti-virals, anti-fungals, anti-inflammatories, anticoagulants, and pro-drugs of these substances.

56. The article of claim 44 wherein said biologically active substance and said polymer form a homogeneous matrix.

57. The article of claim 44 wherein said biologically active substance is encapsulated within said polymer.

58. The article of claim 44 wherein said polymer is characterized by a release rate of the biologically active substance in vivo controlled at least partially as a function of hydrolysis of the phosphoester bond of the polymer upon biodegradation.

59. The article of claim 44 wherein said article is adapted for implantation or injection into the body of an animal.

60. The article of claim 44 wherein said article results in minimal tissue irritation when implanted or injected into vasculated tissue.

61. The article of claim 44 wherein said article is in the form of a laminate for degradable fabric.

62. The article of claim 44 wherein said article is in the form of a biosorbable suture, a material for repairing bone injuries, or a coating on an implant device.

63. A method for the controlled release of a biologically active substance comprising the steps of:
(a) combining the biologically active substance with a biodegradable polymer having the recurring monomeric units shown in formula I:

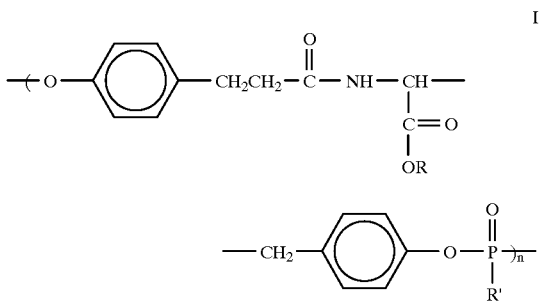

wherein:
R is selected from the group consisting of H, alkyl, aryl, and heterocyclic; and
R' is selected from the group consisting of-H-alkyf, alkoxy, aryl, aryloxy, hetercyclic and heterocycloxy; and
n is 5 to 500,
wherein said biodegradable polymer is biocompatible before and upon biodegradation, to form an admixture;
(b) forming said admixture into a shaped, solid article, and
(c) implanting or injecting said solid article in vivo at a preselected site, such that the solid implanted or injected matrix is in at least partial contact with a biological fluid.

64. The method of claim 63 wherein R is a branched or straight chain alkyl group.

65. The method of claim 63 wherein R' is an alkoxy group.

66. The method of claim 63 wherein the n is 5 to 300.

67. The method of claim 63 wherein said polymer comprises additional biocompatible monomeric units.

68. The method of claim 63 wherein said biologically active substance is selected from the group consisting of polysaccharides, growth factors, hormones, anti-angiogenesis factors and other anti-neoplastic agents, interferons or cytokines, and pro-drugs of these substances.

69. The method of claim 63 wherein said biologically active substance is a therapeutic drug or pro-drug.

70. The method of claim 69 wherein said drug is selected from the group consisting of chemotherapeutic agents, antibiotics, anti-virals, anti-fungals, anti-inflammatories, and anticoagulants.

71. The method of claim 63 wherein said biologically active substance and said polymer form a homogeneous matrix.

72. The method of claim 63 further comprising encapsulating said biologically active substance within said polymer.

73. The method of claim 63 wherein said polymer is characterized by a release rate of the biologically active substance in vivo controlled at least partly as a function of hydrolysis of the phosphoester bond of the polymer upon degradation.

74. The method of claim 63 wherein said article is non-toxic and results in minimal tissue irritation when implanted or injected into vasculated tissue.

75. The method of claim 63 wherein said article is in the form of a laminate for degradable fabric.

76. The method of claim 63 wherein said polymer composition is used as a coating for an implant.

77. The method of claim 63 wherein the polymer composition is used as a barrier for adhesion prevention.

78. The method of claim 63 wherein said polymer composition is fabricated as a tube for nerve generation.

* * * * *